United States Patent [19]

Richardson

[11] Patent Number: 4,886,757
[45] Date of Patent: Dec. 12, 1989

[54] SPIRAMYCIN RESISTANCE-CONFERRING CLONING VECTORS

[75] Inventor: Mark A. Richardson, Indianapolis, Ind.

[73] Assignee: Eli Lilly and Company, Indianapolis, Ind.

[21] Appl. No.: 38,689

[22] Filed: Apr. 15, 1987

[51] Int. Cl.$^4$ .................. C12N 15/00; C12N 1/20
[52] U.S. Cl. ................. 435/252.3; 435/886; 435/172.3; 435/183; 435/235; 435/252.33; 435/252.35; 435/320; 435/849; 435/872; 536/27; 935/9; 935/24; 935/60; 935/72
[58] Field of Search ............... 435/68, 91, 169, 170, 435/172.1, 172.3, 252.3, 320, 886, 872, 27; 536/27; 935/6, 9, 10, 22, 23, 24, 27, 29, 52, 55, 56, 59, 60, 66, 72, 75

[56] References Cited

U.S. PATENT DOCUMENTS 4,753,880 6/1988 Schaus et al. .................. 435/172.3

OTHER PUBLICATIONS

Richardson, et al., 1988, Gene 61:231–241.
Manis et al., Abstracts of the Annual Meeting of the American Society for Microbiology 1984, 84th Annual Meeting, St. Louis, Missouri, p. 119.
Chambers and Hunter, 1984, Biochem. Soc. Trans. 12: 644–645.
Thompson et al., 1982, Gene 20:51–62.
Thompson et al, 1982, J. Bacteriol. 151: 668–677.
Fujisawa and Weisblum, 1981, J. Bacteriol. 146: 621–631.
Murakami et al., 1983, J. Antibiotics 36(10): 1305–1311.
Tohyama et al., 1984, J. Antibiotics 37(12): 1736–1737.
Bibb et al., 1985, Mol. Gen. Genet. 199: 26–36.
Ohnuki et al., 1985, J. Bacteriol. 161(3): 1010–1016.

Primary Examiner—Thomas G. Wiseman
Assistant Examiner—Richard C. Peet
Attorney, Agent, or Firm—Douglas K. Norman; Leroy Whitaker

[57] ABSTRACT

A novel gene conferring resistance to spiramycin in Streptomyces and related organisms was cloned from a genomic library of *Streptomyces ambofaciens* DNA. A thirty-one Kb fragment of *S. ambofaciens* DNA including the spiramycin-resistance gene was isolated from this library on a cosmid designated pKC592. The novel spiramycin-resistance gene can be isolated on an ~2.9 Kb BamHI fragment by subcloning restriction fragments obtained from the pKC592 insert DNA. This BamHI fragment contains all of the information required for the expression of the spiramycin resistant phenotype in Streptomyces. Vectors and transformants containing the novel spiramycin resistance gene are provided.

29 Claims, 13 Drawing Sheets

Restriction Site and Function Map of Plasmid pKC592
(~ 43 kb)

Restriction Site and Function Map of Plasmid pHJL225
(~9.4 kb)

Restriction Site and Function Map of Plasmid pHJL400
(~5.8 kb)

Restriction Site and Function Map of Plasmid pKC631
(~ 8.7 kb)

Restriction Site and Function Map of Plasmid pKC681
(~ 8.5 kb)

Restriction Site and Function Map of Plasmid pKC682
(~ 8.5 kb)

Restriction Site and Function Map of Plasmid pKC1001

Restriction Site and Function Map of Plasmid pKC1002

Restriction Site and Function Map of Plasmid pKC331
(~ 38.1 kb)

Restriction Site and Function Map of Phage pKC1003 (~41 kb)

Restriction Site and Function Map of Phage pKC1004
(~ 41 kb)

SPIRAMYCIN RESISTANCE-CONFERRING CLONING VECTORS

SUMMARY OF THE INVENTION

The present invention comprises a novel spiramycin resistance-conferring gene, designated srmC, recombinant DNA cloning vectors that comprise the gene, and transformats containing the spiramycin resistance conferring vectors. *Streptomyces ambofaciens* produces spiramycin, a macrolide antibiotic consisting of a 16-member cyclic lactone and three sugar residues; mycaminose, mycarose and forosamine, which is used in clinical and veterinary medicine. The antibiotic activity of spiramycin, like other macrolides, is due to inhibition of protein synthesis by a mechanism that involves the binding of spiramycin to the ribosome.

The present invention provides spiramycin resistance-conferring cloning vectors for use in Streptomyces and related organisms. The development and exploitation of recombinant DNA technology in Streptomyces depends upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present invention are particularly useful because they are versatile, selectable, and can be conjugated or transformed in any Streptomyces cell that is sensitive to spiramycin and permissive for Streptomyces replicons or integrating sequences of the vector. In addition, the vector can be made bifunctional and operative in other more convenient host cells such as *E. coli*. Streptomyces provide over half of the clinically important antibiotics and thus is a commercially significant group. The present invention provides new and useful cloning vectors for this industrially important group and allows for the cloning of genes both for increasing the yields of known antibiotics, as well as for the production of new antibiotics and antibiotic derivatives.

The present invention further provides a method for selecting Streptomyces transformants from a background of untransformed cells. The method allows one to add non-selectable DNA to the present vectors, transform Streptomyces with the modified vectors and select spiramycin-resistant transformants containing this otherwise non-selectable DNA. Since transformation is a very low frequency event, such a functional test is a practical necessity for determining which cell(s), of among the millions of cells, has acquired the transforming DNA.

For purposes of the present invention, as disclosed and claimed herein, the following terms are defined below.

Recombinant DNA Cloning Vector—any autonomously replicating or integrating agent, including, but not limited to, plasmids, comprising a DNA molecule to which one or more additional DNA segments can be or have been added.

Replicon—a DNA sequence that controls and allows for autonomous replication of a plasmid or other vector.

Integration Sequence—a DNA sequence that directs a recombinant DNA cloning vector or portion of a vector to integrate into and become part of the chromosomal DNA of a host cell.

Phasmid—a recombinant DNA vector that may act as a phage or as a plasmid.

Transformation—the introduction of DNA into a recipient host cell that changes the genotype and results in a change in the recipient cell.

Transformant—a recipient host cell that has undergone transformation.

Transfectant—a recipient host cell that has undergone transformation by phage DNA.

Sensitive Host Cell—a host cell that cannot grow without a DNA segment encoding a selectable resistance characteristic.

Restriction Fragment—any linear DNA molecule generated by the action of one or more restriction enzymes.

$Am^R$—the apramycin-resistant phenotype.
$Ap^R$—the ampicillin-resistant phenotype.
cos—the phage lambda cohesive end sequences.
In the figures, "c" denotes the left cos and "." denotes the right cos end.
$Nm^R$—the neomycin-resistant phenotype.
ori of rep—a plasmid origin of replication.
$Sr^R$—the spiramycin-resistant phenotype.
$Tc^R$—the tetracycline-resistant phenotype.
$Ts^R$—the thiostrepton-resistant phenotype.
srmC—the spiramycin C resistance-conferring gene.

DETAILED DESCRIPTION OF THE INVENTION

The present invention is a recombinant DNA cloning vector which comprises
 (a) a DNA sequence selected from the group consisting of an origin of replication and an integration sequence, (b) a spiramycin C resistance gene that confers resistance to antibiotic spiramycin, subject to the limitation that said origin of replication and integration sequence are functional in Streptomyces and Nocardia.

The present invention can be constructed by ligating the spiramycin C resistance gene (SrmC) containing ~2.9 kb BamHI fragment of plasmid pKC592 into BamHI-digested plasmid pHJL400 to form plasmid pKC631. Plasmid pKC592 can be obtained from *E. coli* K12 DH5/pKC592, a strain deposited and part of the permanent stock culture collection of the Northern Regional Research Laboratory (NRRL), Agricultural Research Service, 1815 North University Street, U.S. Department of Agriculture, Peoria., Ill. 61604. It is available to the public as a source and stock reservoir of the plasmid under the accession number NRRL B-18186. Plasmid pHJL400 is constructed in accordance with the detailed teaching of Example 9 and as earlier disclosed in U.S. Ser. No. 841,920, filed Mar. 20, 1986, Attorney Docket Number X-6786A.

Skilled artisans will readily recognize that for certain purposes and under certain conditions it is more convenient to propagate cloning vectors in *E. coli* than in Streptomyces and related organisms. Consequently, the vectors of the present invention can be modified to be bifunctional shuttle vectors operable in both *E. coli* and Streptomyces. This is done by providing an appropriate *E. coli* origin of replication and selectable sequence to the Streptomyces spiramycin resistance-conferring vectors described above. Thus, the present invention further comprises recombinant DNA cloning vectors which additionally comprise (a) an *E. coli* origin of replication, and
(b) a DNA sequence that confers a selectable phenotype in *E. coli*.

Plasmid pKC592 is an illustrative bifunctional shuttle vector that contains srmC, a Streptomyces replicon, an *E. coli* replicon, and an apramycin resistance gene that confers a selectable phenotype in both Streptomyces and *E. coli*. It can be obtained from *E. coli* K12 DH5/pKC592, which has been deposited at NRRL as described above.

The present vectors comprise a novel spiramycin C resistance gene that was isolated from a known strain of *Streptomyces ambofaciens* (NRRL 15263). Other spiramycin resistance genes (i.e., spiramycin A and spiramycin B) are known, but do not share significant homology to spiramycin C; therefore they are not within the scope of this invention. The present gene confers resistance to the macrolide antibiotic spiramycin and, in some cases, simultaneously to other antibiotics as well. Such cross resistance for certain antibiotic resistance genes is a known phenomenon reported by several authors, including Fujisawa and Weisblum, *J. Bacteriology* 146: 621 (1981).

Figure 2:
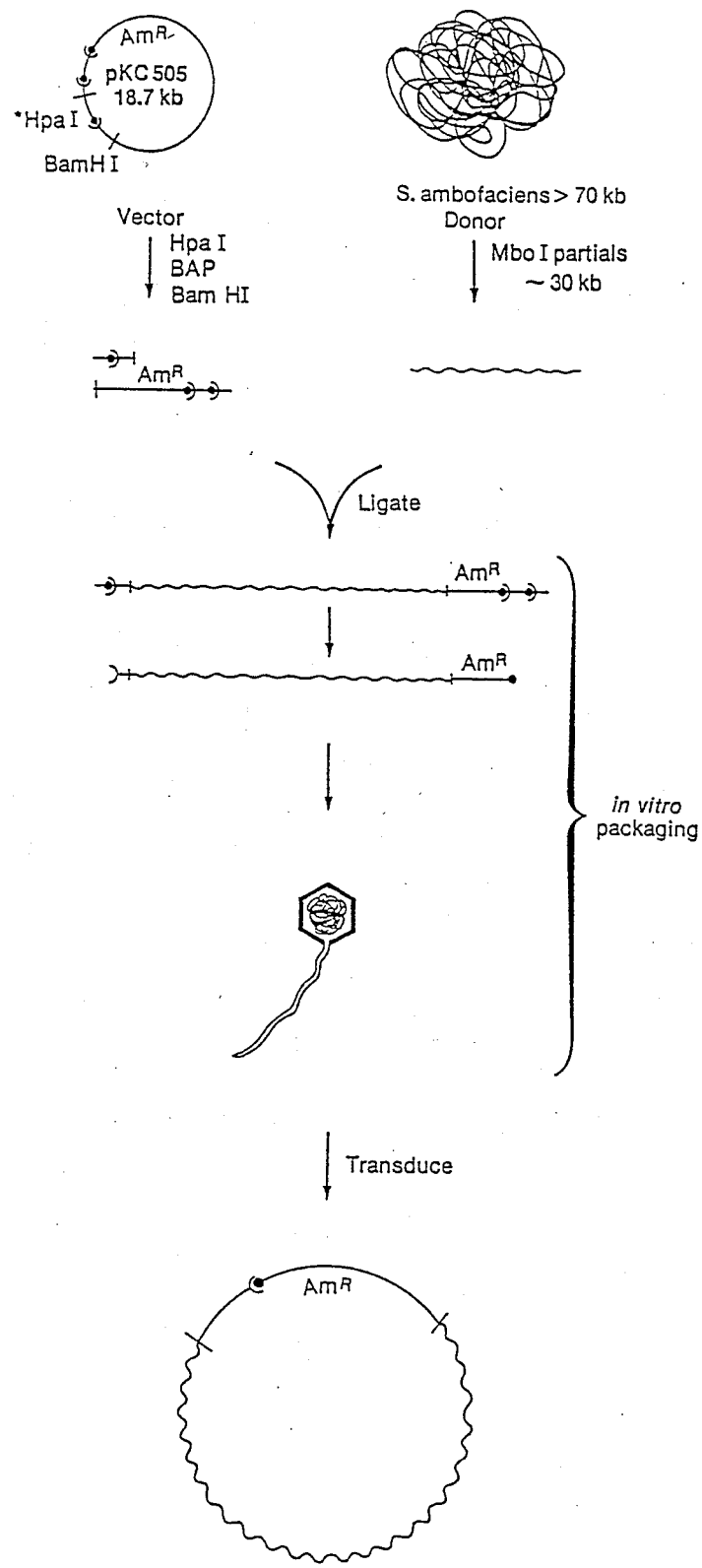
FIG. 2 is a schematic outline of the construction of genomic DNA libraries utilizing cosmid pKC505 and *Streptomyces ambofaciens* DNA.

The present spiramycin C resistance gene was isolated from a Streptomyces gene bank by treating *S. ambofaciens* DNA with MboI restriction enzyme under partial digestive conditions to generate DNA fragments with an average size of ~30 kb. The fragments were then ligated into cosmid pKC505, to derive vectors illustrative of the present invention. A schematic outline of the construction of genomic DNA libraries utilizing cosmid pKC505 and *S. ambofaciens* DNA is provided in FIG. 2 of the accompanying drawings. Cosmid pKC505 is a bifunctional shuttle vector comprising an *E. coli* replicon, the SCP2* Streptomyces replicon and fertility functions, three bacteriophage λ cos sites, and an apramycin resistance gene. It is an ideal vector for constructing SrmC-containing derivative plasmids such as the aforementioned derivative pKC592.

This was done by treating cosmid pKC505 with the restriction enzyme HpaI to generate linear blunt ended fragments. The resultant HpaI ends were dephosphorylated and the fragments subsequently cut with BamHI restriction enzyme generating a small fragment with a single λ cos site and a larger fragment with two λ cos sites (see FIG. 2 of the accompanying drawings for further details). Both fragments, therefore, have one dephosphorylated blunt end (non-ligatable) and another phosphorylated cohesive GATC end (ligatable to the ends generated by MboI digestion).

The DNA fragments from pKC505 and those from *Streptomyces ambofaciens* were mixed and ligated with T4 DNA ligase. The insert DNA is thus flanked by the two vector fragments and the ligated DNA packaged in vitro into bacteriophage λ particles (cosmids). The packaged cosmids were then transduced into *E. coli* K12 SF8, selecting for apramycin resistance, and the resulting *E. coli* transformants pooled to make a primary plasmid pool. The DNA from the primary pool (library) was analyzed structurally to insure that the cloned library contained the desired sequences and also functionally, by transforming into a suitable Streptomyces host. Thus, the pooled plasmid DNA was used to transform *S. griseofuscus*, selecting for apramycin resistance, and then all resistant colonies were pooled, grown up in liquid media, and plated and selected for the spiramycin resistance phenotype. Plasmids from the spiramycin resistant colonies were found to be identical and, upon restriction enzyme analysis, were designated as pKC592.

Figure 6:
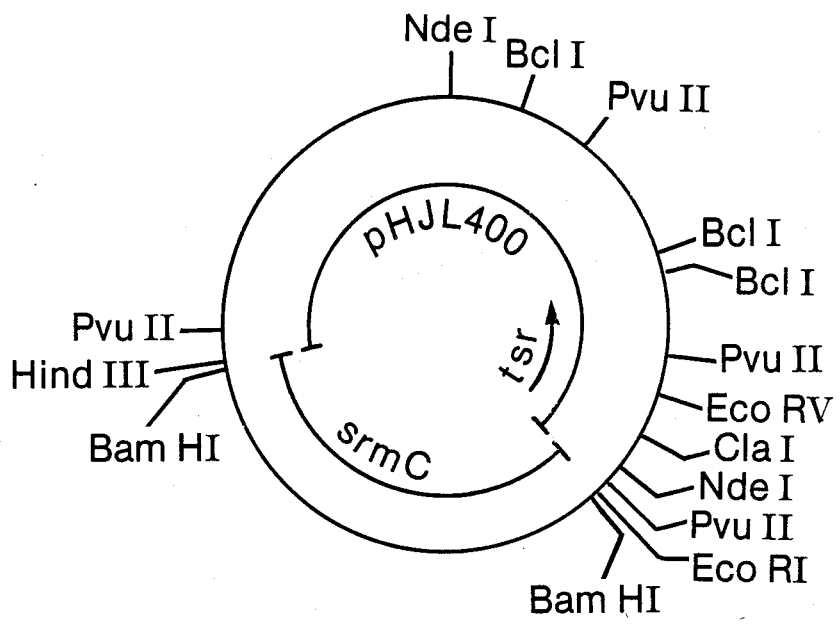
FIG. 6 shows the restriction site and function map of plasmid pKC631.

Various derivative vectors were constructed by digesting illustrative plasmid pKC592 with BamHI restriction enzyme and ligating the resulting ~1.5, ~1.7, ~1.8, ~2.1, ~2.9, ~5.5 and ~9.4 kb fragments into the BamHI site of the aforementioned pHJL400. The resulting vectors were used to transform *Streptomyces griseofuscus* and revealed that the srmC gene is located in the ~2.9 kb BamHI fragment. A derivative plasmid containing the ~2.9 kb was designated as plasmid pKC631. The aforementioned vector comprises the srmC gene and thus further exemplifies the present invention. A restriction site and function map of plasmid pKC631 is presented in FIG. 6 of the accompanying drawings.

The ~2.9 kb srmC gene-containing restriction fragment can also be cloned into conventional Streptomyces vectors which contain only a Streptomyces replicon. For example, the ~2.9 kb BamHI fragment can be ligated into the single BamHI site of plasmid pIJ702 to form plasmids pKC681 and pKC682, which differ only in the orientation of the SrmC fragment. These plasmids, when transformed into Streptomyces spp, can confer spiramycin resistance to a spiramycin sensitive host. Plasmid pIJ702 can be obtained from *Streptomyces lividans*/pIJ702, a strain deposited and made part of the permanent stock culture collection of the American Type Culture Collection (ATCC), Rockville, Md., 20852. It is available to the public as a source and stock reservoir of the plasmid under the accession number ATCC 39155. Restriction site and function maps of plasmids pKC681 and pKC682 are respectfully presented in FIGS. 7 and 8 of the accompanying drawings.

Figure 9:
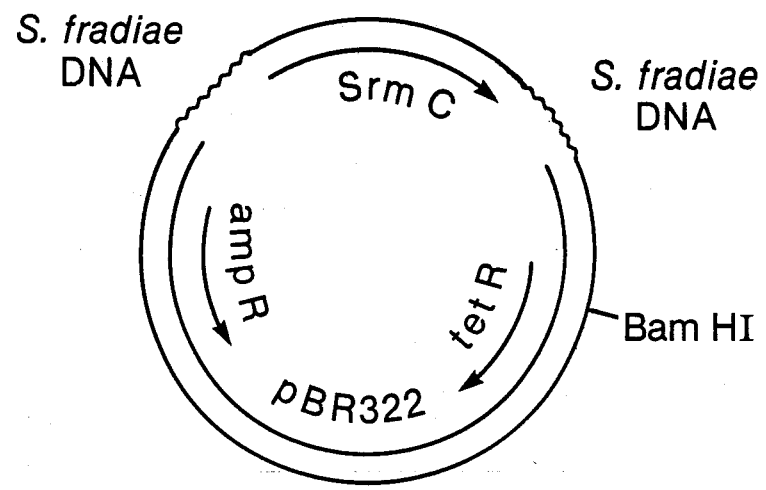
FIG. 9 shows the restriction site and function map of plasmid pKC1001.
Figure 10:
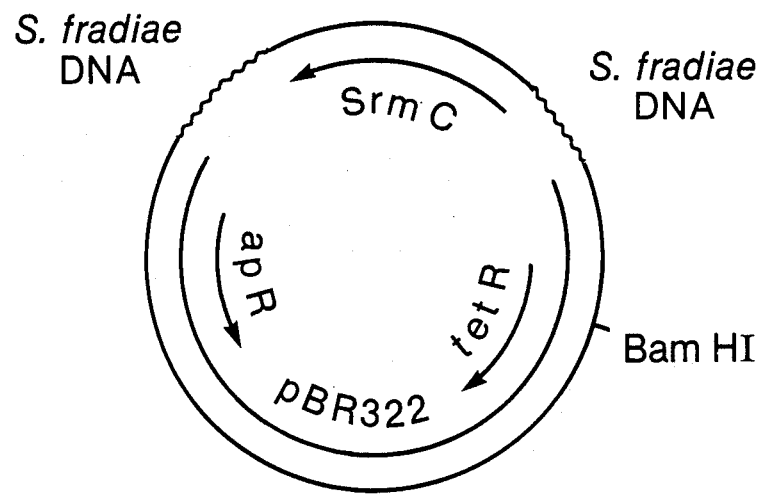
FIG. 10 shows the restriction site and function map of plasmid pKC1002.

The ~2.9 kb srmC gene-containing restriction fragment can further be used to confer spiramycin resistance to a sensitive host via homologous recombination and integration into the host's genome. For example, Streptomyces fradiae (ATCC 19609) can be partially digested with MboI restriction enzyme and then the 5' overhangs filled-in using DNA Polymerase I. This DNA is then ligated into EcoRI cut, filled-in plasmid pBR322 (BRL) and transformed into E. coli JM109 cells (Stratogene), selecting for tetracycline resistance. The resultant plasmid is then partially digested with BamHI restriction enzyme and the ~2.9 kb srmC gene-containing fragment from pKC592 is then ligated into the BamHI sites. Upon transformation into E. coli and selection on tetracycline plates, only those plasmids which have the srmC gene cloned into the S. fradiae DNA in the plasmid survive. The surviving transformants are pooled and the plasmids, which differ only in the orientation of the srmC fragment, are designated pKC1001 and pKC1002. When back-transformed into Streptomyces fradiae, these plasmids cannot autonomously replicate because they contain no Streptomyces replicon. Therefore the only resistant colonies which arise are those which grow from cells in which a homologous recombination and subsequent integration event has occurred. Restriction site and function maps of plasmids pKC1001 and pKC1002 are respectively presented in FIGS. 9 and 10 of the accompanying drawings. It should be noted that even when the srmC gene is carried on a plasmid which contains a Streptomyces replicon, a low, but still detectable, number of integration events may still occur in any culture. Therefore, an autonomously replicating vector might also integrate, albeit at a low frequency.

Figure 11:
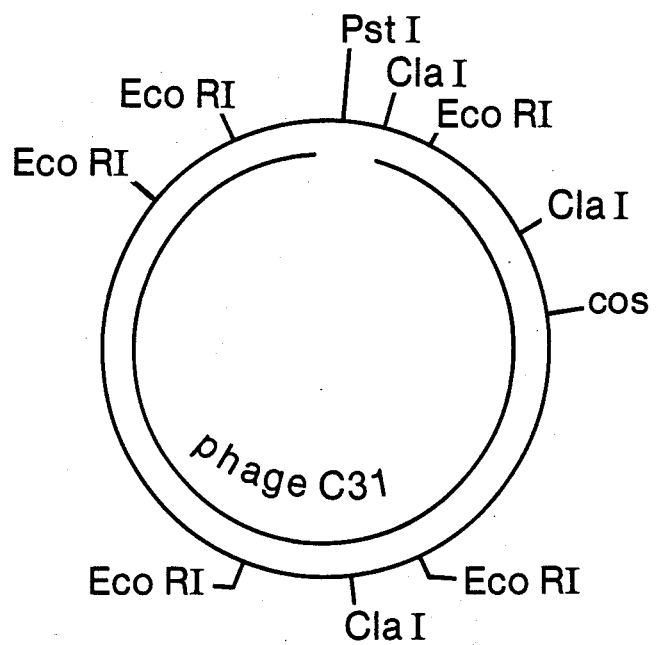
FIG. 11 shows the restriction site and function map of plasmid pKC331.
Figure 12:
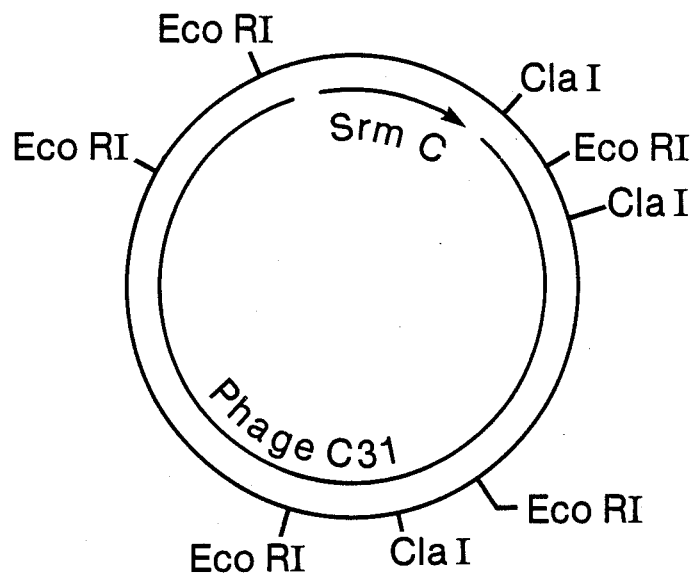
FIG. 12 shows the restriction site and function map of phage pKC1003.
Figure 13:
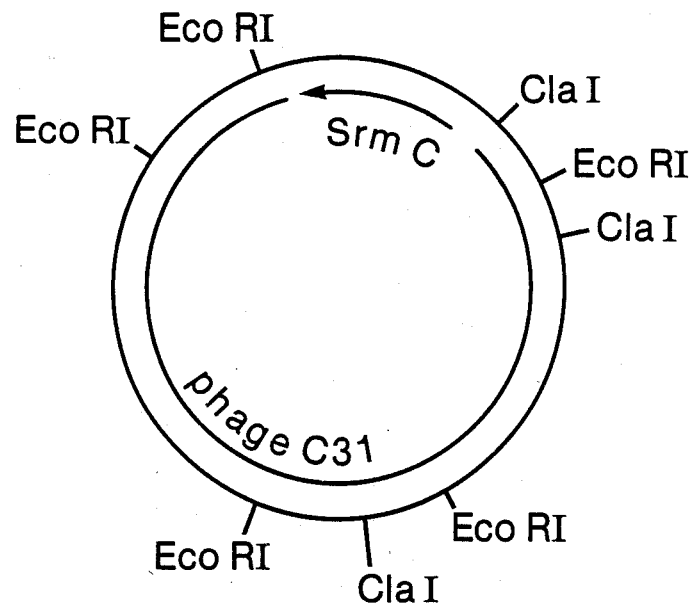
FIG. 13 shows the restriction site and function map of phage pKC1004.

The srmC gene can also be used to construct illustrative vectors other than plasmids. For example phage φC31 is a well known Streptomyces phage that is an excellent starting material for constructing certain other integrative vectors. A derivative of phage φC31, plasmid pKC331, is especially preferred for constructing such integrating vectors and can be obtained from E. coli K12 BE447/pKC331, a strain deposited and made part of the permanent stock culture collection of the aforementioned Northern Regional Research Laboratory under the accession number NRRL B-15828. A restriction site and function map of plasmid pKC331 is presented in FIG. 11 of the accompanying drawings. Ligation of the ~37 Kb PstI restriction fragment of plasmid pKC331 to the ~2.9 Kb spiramycin resistance-conferring BamHI restriction fragment of plasmid pKC592, (after 5' overhangs of both fragments are filled in using DNA polymerase I), results in the derivative phages pKC1003 and pKC1004, which differ only in the orientation of the srmC gene. These phages are integrative vectors which confer spiramycin resistance to Streptomyces and thus further exemplify the present invention. Restriction site and function maps of phages pKC1003 and pKC1004 are respectfully presented in FIGS. 12 and 13 of the accompanying drawings.

It will be understood that the SrmC gene-containing restriction fragments are not limited to a particular vector or a position on a cloning vector. For example, the spiramycin resistance gene can be subcloned into other known vectors such as the pSCP103-derived plasmids (Lydiate et al., 1985, Gene 35:223), the pFJ103-derived plasmids (Richardson et al., 1982, Gene 20:451), and pHJL400 (Hesshberger et al. 1986, Plasmid 15:199–209), to name a few. Those skilled in the art understand or can readily determine which vector is desirable for a specific purpose and which sites on a vector are advantageous for the ligation or insertion of a particular spiramycin resistance gene-containing restriction fragment. In addition, molecular linkers can be provided, thereby creating specific sites for DNA subcloning, or the fragment can be modified by adding, eliminating or substituting certain nucleotides to alter characteristics and provide a variety of restriction sites for ligation of DNA. Those skilled in the art understand nucleotide chemistry and the genetic code and thus which DNA modifications are desirable for a specific purpose.

Although illustrative plasmid pKC592 comprises the SCP2* Streptomyces replicon derived from cosmid pKC505, a variety of other Streptomyces replicons can also be substituted to construct similar vectors. Table 1 is an illustrative, but not comprehensive, listing of Streptomyces plasmids from which additional, functional Streptomyces replicons can be obtained. Those skilled in the art recognize that all or part of the plasmids may be used to construct vectors exemplifying the present invention so long as the replicon function is not disrupted. The plasmid-containing host and depository accession number are also listed in Table 1.

TABLE I

| Streptomyces Plasmids | | |
|---|---|---|
| Plasmid | Host | Accession Number |
| SCP2 | Streptomyces coelicolor A3(2) | NRRL 15042 |
| pEL7 | Streptomyces ambofaciens | NRRL 12523 |
| SLP1 | Streptomyces lividans | NCIB[1] 11417 |
| pNM100 | Streptomyces virginiae | NRRL 15156 |
| pEL103 | Streptomyces granuloruber A39912.13/pEL103 | NRRL 12549 |
| pIJ702 | Streptomyces lividans | ATCC[2] 39155 |

Other replicons such as SLP1.2 (Horinouchi et al., 1985, J. Bacteriol. 162:406), pSRC1-b (Shindoh et al., 1984, J. Antibiot. 37:512), pSL1 (Nakano et al., 1982, FEMS Microbiol. Lett. 13:279) and pSF765 (Murakami et al., 1983, J. Antibiot. 36:429) may also be used and are therefore within the scope of the present invention.
[1]National Collection of Industrial Bacteria (NCIB), Torry Research Station, Post Office Box 31, 135 Abbey Road, Aberdeen AB98DG, Scotland, United Kingdom
[2]American Type Culture Collection (ATCC), 12301 Parklawn Drive, Rockville, Maryland 20582, United States of America The vectors of the present invention comprise a Streptomyces replicon, a spiramycin resistance-conferring restriction fragment and optionally, an E. coli replicon and selectable sequence. Because amplification and manipulation of plasmids is done faster and more efficiently in E. coli than in Streptomyces, the presence of an E. coli replicon is advantageous and adds to the general utility of the present illustrative vectors. In fact, the wealth of genetic and biochemical information about E. coli makes it a convenient host cell for purposes of the present invention. However, the invention is not limited to any one species or strain but can be used with any organism where the E. coli replicon is functional. Since the presence of a particular E. coli replicon is not a critical component of the present vectors, the substitution of functional replicon-containing and, if desired, antibiotic resistance-conferring restriction fragments from E. coli plasmids such as, for example, pCZ101 (Schoner et al., 1984, Proc. Natl. Acad. Sci. U.S.A. 81:5403), pACYC184, pBR325, pBR328 and the like is within the scope of the present invention. A number of other host cells are exemplified throughout the specification and examples and will be apparent to those skilled in the art.

The recombinant DNA cloning vectors of the present invention are also not limited for use in a single species or strain of Streptomyces. To the contrary, the vectors are broadly applicable and can be used with spiramycin-sensitive host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well known in the art (Lomovskaya et al., 1980, *Microbiology Reviews* 44:206). Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless.

The srmC gene can be used to transform a variety of spiramycin-sensitive organisms to spiramycin resistance. In organisms naturally sensitive to macrolide antibiotics, including spiramycin, the srmC gene can be used as a genetic marker while in organisms that produce one or more macrolide antibiotics yet are sensitive to low levels of macrolide antibiotic, the vectors of the present invention can be used to increase or augment the organism's natural resistance. Preferred host cells of restrictionless strains of spiramycin-sensitive Streptomyces taxa, and in which the present vectors may be transformed, include restrictionless cells of, for example: *Streptomyces coelicolor, S. granuloruber, S. roseosporus, S. acrimycins, S. glaucescens, S. parvilin, S. pristinaespiralis, S. violaceoruber, S. vinaceus, S. espinosus, S. azureus, S. griseofuscus, S. fradiae* and *S. toyocaensis.*

The following Tables present a representative sampling of various other antibiotic-producing organisms in which the srmC gene can also be used.

TABLE II

| Aminocyclitol Antibiotic-Producing Organisms | |
|---|---|
| Organism | Antibiotic |
| Bacillus | |
| various species | various aminocyclitols |
| Micromonospora | |
| various species | gentamycins |
| Saccharopolyspora | |
| various species | various aminocyclitols |
| Streptomyces | |
| albogriseolus | neomycins |
| albus var. metamycinus | metamycin |
| aquacanus | N—methyl hygromycin B |
| atrofaciens | hygromycins |
| bikiniensis | streptomycin |
| bluensis var. bluensis | bluensomycin |
| canus | ribosyl paromamine |
| catenulae | catenulin |
| chrestomyceticus | aminosidine |
| crystallinus | hygromycin A |
| erythrochromogenes | |
| var. narutoensis | streptomycin |
| eurocidicus | A16316-C |
| fradiae | hybrimycins and neomycins |
| fradiae var. italicus | aminosidine |
| galbus | streptomycin |
| griseus | streptomycin |
| griseoflavus | MA 1267 |
| hofuensis | seldomycin complex |
| hygroscopicus | hygromycins, leucanicidin, and Hygrolidin |
| hygroscopicus forma glebosus | glebomycin |
| hygroscopicus var. | |

TABLE II-continued

| Aminocyclitol Antibiotic-Producing Organisms | |
|---|---|
| Organism | Antibiotic |
| limoneus | validamycins |
| hygroscopicus var. sagamiensis | spectinomycin |
| kanamyceticus | kanamycin A and B |
| kasugaensis | kasugamycins |
| kasugaspinus | kasugamycins |
| lavendulae | neomycin |
| lividus | lividomycins |
| mashuensis | streptomycin |
| microsporeus | SF-767 |
| netropsis | LL-AM31 |
| noboritoensis | hygromycins |
| olivaceus | streptomycin |
| olivoreticuli var. cellulophilus | destomycin A |
| poolensis | streptomycin |
| rameus | streptomycin |
| ribosidificus | SF733 |
| rimofaciens | destomycin A |
| rimosus forma paromomycinus | paromomycins and catenulin |
| spectabilis | spectinomycin |
| tenebrarius | tobramycin and apramycin |
| Streptoverticillium | |
| flavopersicus | spectinomycin |

TABLE III

| Ansamycin Antibiotic-Producing Organisms | |
|---|---|
| Organism | Antibiotic |
| Micromonospora | |
| various species | various ansamycins |
| Nocardia | |
| mediterranei | rifamycin |
| Streptomyces | |
| collinus | ansatrienes and napthomycins |
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotrienes |
| sp. E88 | mycotrienes |
| spectabilis | streptovaricins |
| tolypophorous | tolypomycin |

TABLE IV

| Anthracycline and Quinone Antibiotic-Producing Organisms | |
|---|---|
| Organism | Antibiotic |
| Streptomyces | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromogenes | arugomycin |

TABLE V

β-Lactam Antibiotic-Producing Organisms

| Organism | Antibiotic |
|---|---|
| Cephalosporium | |
| various species | various β-lactams |
| Nocardia | |
| lactamadurans | cephamycin C |
| Penicillium | |
| various species | various β-lactams |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B |
| halstedi | cephamycin A and B |
| heteromorphus | C2081X and cephamycin A and B |
| hygroscopicus | deacetoxycephalosporin C |
| lipmanii | penicillin N, 7-methoxycephalosporin C, A16884, MM4550, and MM13902 (MM17880) epithienamycin F, MM 4550, and MM 13902 |
| olivaceus | |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

TABLE VI

Macrolide, Lincosamide, and Streptogramin Antibiotic-Producing Organisms

| Organism | Antibiotic |
|---|---|
| Micromonospora | |
| rosaria | rosaramicin |
| Streptomyces | |
| albireticuli | carbomycin |
| albogriseolus | mikonomycin |
| albus | albomycetin |
| albus var. | |
| coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |

TABLE VI-continued

Macrolide, Lincosamide, and Streptogramin Antibiotic-Producing Organisms

| Organism | Antibiotic |
|---|---|
| fungicidicus | NA-181 |
| fungicidicus var. | |
| espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A₃ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A₃ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE VII

Miscellaneous Antibiotic-Producing Streptomyces

| Antibiotic Type | Streptomyces Species | Antibiotic |
|---|---|---|
| amino acid analogues | sp. | cycloserine |
| cyclopentane ring-containing | coelicolor | methylenomycin A |
| | erythrochromogenes | sarkomycin |
| | violaceoruber | methylenomycin A |
| nitro-containing | venezuelae | chloramphenicol |
| polyenes | griseus | candicidin |
| | nodosus | amphotericin B |
| | noursei | nystatin |
| tetracyclines | aureofaciens | tetracycline, chlortetracycline, demethyltetracycline, and demethylchlortetracycline |
| | rimosus | oxytetracycline |

TABL3 VIII

Nucleoside Antibiotic-Producing Organisms

| Organism | Antibiotic |
|---|---|
| Corynebacterium | |

TABLE VIII-continued

Nucleoside Antibiotic-Producing Organisms

| Organism | Antibiotic |
| --- | --- |
| michiganese pv. rathayi | tunicamycin analogues |
| Nocardia | |
| candidus | pyrazofurin |
| Streptomyces | |
| antibioticus | ara-A |
| chartreusis | tunicamycin |
| griseoflavus var. | |
| thuringiensis | streptoviridans |
| griseolus | sinefungin |
| lysosuperificus | tunicamycin |

TABLE IX

Peptide Antibiotic-Producing Organisms

| Organism | Antibiotic |
| --- | --- |
| Actinoplanes | |
| missouriensis | actaplanin |
| teichomyceticus | teicoplanin |
| Bacillus | |
| various species | bacitracin, polymixin, and colistin |
| Nocardia | |
| candidus | A-35512 and avoparcin |
| lurida | ristocetin |
| orientalis | vancomycin |
| Streptomyces | |
| antibioticus | actinomycin |
| aureus | thiostrepton |
| canus | amphomycin |
| eburosporeus | LL-AM374 |
| haranomachiensis | vancomycin |
| pristinaespiralis | pristinamycin |
| roseosporus | lipopeptides, such as A21978C |
| toyocaensis | A47934 |
| virginiae | A41030 |

TABLE X

Polyether Antibiotic-Producing Organism

| Organism | Antibiotic |
| --- | --- |
| Actinomadura | |
| various species | various polyethers |
| Dactylosporangium | |
| various species | various polyethers |
| Nocardia | |
| various species | various polyethers |
| Streptomyces | |
| albus | A204, A28695A and B, and salinomycin |
| aureofaciens | narasin |
| cacaoi var. | |
| asoensis | lysocellin |
| chartreusis | A23187 |
| cinnamonensis | monensin |
| conglobatus | ionomycin |
| eurocidicus var. | |
| asterocidicus | laidlomycin |
| flaveolus | CP38936 |
| gallinarius | RP 30504 |
| griseus | grisorixin |
| hygroscopicus | A218, emericid, DE3936, A120A, A28695A and B, etheromycin, and dianemycin |
| lasaliensis | lasalocid |
| longwoodensis | lysocellin |
| mutabilis | S-11743a |
| ribosidificus | lonomycin |
| violaceoniger | nigericin |
| Streptoverticillium | |
| various species | various polyethers |

The vectors of the present method confer spiramycin resistance to the spiramycin-sensitive Streptomyces and related host cells described above. Although 25 µg/ml of spiramycin is generally toxic to spiramycin-sensitive Streptomyces, vectors of the present invention confer resistance to levels approaching 100 µg/ml of spiramycin. The preferred spiramycin concentration for purposes of selection for Streptomyces species is readily determined by procedures well known in the art. While all embodiments of the present invention are useful, some of the vectors and transformants are preferred. Accordingly, Streptomyces griseofuscus is the preferred host for both preferred plasmids pKC592 and pKC631.

The recombinant DNA vectors of the present invention have broad utility and help fill the need for suitable cloning vehicles for use in Streptomyces and related organisms. More particularly, the present vectors are used as a means for selecting a recombinant DNA-containing Streptomyces host cell. This is accomplished by transforming a spiramycin-sensitive, preferably restrictionless Streptomyces host cell with one of the present vectors, such as pKC631, and culturing the transformed cell under conditions suitable for selection for spiramycin resistance. Moreover, the ability of the present vectors to confer spiramycin resistance provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the non-selectable DNA can be isolated by spiramycin selection. Such non-selectable DNA segments can be inserted at any site, except within regions necessary for plasmid function and replication or within the spiramycin resistance-conferring gene, and include, but are not limited to, genes that specify antibiotic modification enzymes and regulatory genes of all types.

The spiramycin resistance-conferring vectors of the present invention are also useful for ensuring that linked DNA segments are stably maintained in host cells over many generations. These genes or DNA fragments, covalently linked to the spiramycin resistance-conferring restriction fragment and propagated in Streptomyces, are maintained by exposing the transformants to levels of spiramycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The method, vectors and transformants of the present invention provide for the cloning of genes to improve yields of various products that are currently produced in Streptomyces and related cells. Examples of such products include, but are not limited to, Streptomycin, Cephalosporins, Actaplanin, Apramycin, Narasin, Monensin, Tobramycin, Erythromycin and the like. The present invention also provides selectable vectors that are useful for cloning, characterizing and reconstructing DNA sequences that code for commercially important proteins such as, for example, human insulin, human proinsulin, glucagon, interferon and the like; for enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, Streptomycin, Cephalosporin, Apramycin, Actaplanin, Narasin, Tobramycin, Monensin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonium, calcium, phosphate, chloride, sulfate and like ions. As is necessary for the growth and development of other microorganisms, essential trace elements are also added. Such trace elements are commonly supplied as impurities incidental to the addition of other constituents of the medium. Specific culture media are disclosed in the examples and, as is known, Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

Escherichia coli K12 strains can also be cultured in a number of ways using any of several different media. Carbohydrate sources which are preferred in a culture medium include glucose and glycerol; nitrogen sources include ammonium salts, amino acid mixtures, and peptones. Nutrient inorganic salts are also incorporated and include those listed for Streptomyces, as well as salts yielding magnesium ions. E. coli can be grown under aerobic culture conditions over a pH range of 6.5 to 7.5 at temperatures ranging from about 25° to 42° C. For plasmid stability maintenance, it is desirable to start with a culture medium at a pH of about 7.2 and maintain a culture temperature of about 30° C.

EXAMPLE 1

Culture of E. coli K12 DH1/pKC420 and Isolation of Cosmid pKC420

Five ml cultures of E. coli K12 DH1/pKC420 (NRRL B-15837) were grown under selective conditions in TY media (1% tryptone, 0.5% yeast extract, 0.5% sodium chloride pH 7.4) according to conventional microbiological procedures. The cells were spun in a table top centrifuge and the pellet resuspended in 1 ml of 0.3 M sucrose, 25 mM EDTA (ethylenediaminetetraacetate) and 25 mM Tris-HCl pH 8 (Solution I). After transfer to an Eppendorf tube, the cells were centrifuged for about one minute and the pellet was resuspended in 0.5 ml of Solution I. About 50 $\mu$l of freshly made lysozyme (20 mg/ml in water) were added and the solution was incubated for 10 minutes at 37° C.

After the addition of 250 $\mu$l of freshly made lysin mix (2% sodium dodecyl sulfate and 0.3 N NaOH), the cells were immediately and completely vortexed. The cells were then incubated for ten minutes at 50° C., cooled and 100 $\mu$l of phenol-Sevag (phenol-chloroformisoamyl alcohol, 25-24-1) was added. The tube was vortexed for one minute. The DNA was centrifuged for two minutes in an Eppendorf centrifuge and the supernatant was pipetted and transferred to another tube with 70 $\mu$l of unbuffered 3 M sodium acetate and 0.7 ml of isopropanol to precipitate the DNA. This solution was incubated for five minutes at room temperature and then centrifuged for two minutes. The supernatant was gently and completely decanted to remove all the excess liquid.

The DNA precipitate was redissolved in 500 $\mu$l of TE (10 mM Tris-HCl pH8 and 1 mM EDTA) and 25 $\mu$l of 100 mM Spermine HCl were added. This mixture was vortexed and then incubated for five minutes at room temperature before a five minute spin in an Eppendorf centrifuge. The supernatant was again completely decanted and discarded and the precipitated DNA was vortexed with 300 $\mu$l of 0.3 M sodium acetate, 10 mM magnesium acetate and 700 $\mu$l of 95% ethanol. This solution was incubated for five minutes at room temperature and the DNA collected as above. The pellet was redissolved in 10 $\mu$l of TE and constituted the desired cloning vehicle.

EXAMPLE 2

Construction of Plasmid pHJL202

The plasmid pHJL202 contains the streptomyces replicon from plasmid SCP2* (Bibb et al., 1977, *Molec. Gen. Genet.* 154:155), as well as neomycin resistance and ampicillin resistance genes. The construction of pHJL202 is described below.

A. Partial KpnI Digestion of Plasmid pJL192

About 13 $\mu$l (~3.25 $\mu$g) of plasmid pJL192 DNA, isolated from E. coli K12 C600R$_K$-M$_K$-/pJL192 (NRRL B-15040) and prepared according to the teaching of Example 1, 25 $\mu$l water, 5 $\mu$l BSA (Bovine Serum Albumen 1 mg/ml), 5 $\mu$l 10X KpnI restriction buffer (60 mM Tris-HCl pH 7.5, 60 mM NaCl, 60 mM MgClz) and 2 $\mu$l KpnI enzyme* were mixed and incubated at 37° C. for 45 minutes. A 10 $\mu$l aliquot was removed, mixed with 40 $\mu$l water and heated at 70° C. for 10 minutes to inactivate the enzyme. This protocol produces all possible reaction products ranging from molecules that have not been cleaved by the KpnI restriction enzyme to those that have been completely digested by the KpnI restriction enzyme. The aliquot was precipitated with 1/10 volume 3M NaOAc pH 8 and 2 volumes ethanol and then frozen at $-70°$ C. for 1 hour.

·Ligation

The precipitate was collected, washed twice, air dried and then resuspended in 20 $\mu$l water. About 6 $\mu$l of the reaction was removed and mixed with a solution of 20 $\mu$l 5X kinase/ligase buffer (250 mM Tris-HCl pH 7.8, 25% Glycerol, 25 mM Dithiothreitol, and 50 mM MgCl$_2$) 40 $\mu$l 0.66 M ATP pH 7.4, 33 $\mu$l water and 1 $\mu$l T4 DNA ligase and incubated at 15° C. for 72 hours to promote self-circularization. After incubation, 50 $\mu$l were removed from the reaction and the reaction was terminated by increasing the temperature at 70° C. for 10 minutes. The reaction products were precipitated as above and resuspended in 15 $\mu$l water.

*Restriction and other enzymes can be readily obtained from the following sources:
New England Biolabs, Inc., 32 Tozer Road, Beverly, Mass. 01915
Bethesda Research Laboratories, Inc., P.O. Box 577, Gaithersburg, Md. 20760
Boehringer Mannheim Biochemicals, P.O. Box 50816, Indianapolis, Ind. 46250

C. Transformation

Frozen, competent *E. coli* K12 C600R$_K$-M$_K$- (ATCC 33525) cells were thawed in an ice bath and mixed in a ratio of 0.1 ml of cells to 0.05 ml of plasmid DNA and 37.5 μl of 0.1X SSC 0.015M NaCl, 0.0015M Sodium Citrate at pH 7). The transformation mixture was chilled on ice for 20 minutes, heat shocked at 42° C. for 1 minute and chilled on ice for another 10 minutes. The samples were then diluted with 0.85 ml of TY-broth, incubated at 37° C. for 1.5 hours, spread on TY-agar* containing ampicillin (50 μg/ml) and incubated for 18 hours at 37° C. The resulting colonies of correct phenotype, ampicillin resistant (Ap$^R$) and tetracycline sensitive (Tc$^S$) were screened for plasmid size in substantial accordance with the method of in-the-well-lysis as described by Eckhardt et al., 1978, *Plasmid* 1:584 (1978). The ampicillin resistant and tetracycline sensitive colonies containing the desired ~18 kb plasmid, designated as pHJL202, were isolated according to known procedures, cultured, and conventionally identified by restriction enzyme and agarose gel electrophoretic (AGE) analysis of the constitutive plasmids. The identified *E. coli* K12 C600R$_K$-M$_K$-pHJL202 transformants were then used for subsequent production and isolation of plasmid pHJL202 in substantial accordance with the teaching of Example 1.

*TY-agar was prepared by adding 15 g Bacto-agar to each liter of TY broth before autoclaving.

EXAMPLE 3
Construction of Cosmid pKC473

To obtain the cosmid backbone used in the construction of cosmid pKC473, pKC420 DNA is digested with EcoRI and BamHI restriction enzymes. About 10 μl of pKC420 DNA, prepared according to the teaching of Example 1, 25 μl water, 5 μl BSA, 5 μl 10X EcoRI restriction buffer (1M Tris-HCl pH 7.5, 0.5M NaCl, 0.1M MgCl$_2$) and 2 μl EcoRI enzyme are mixed, incubated at 37° C. for 1 hour, and then heated at 70° C. for 10 minutes to inactivate the enzyme. The mixture is precipitated with 1/10 volume 3 M NaOAC, pH 8.0 and 2 volumes ethanol and then frozen at −70° C. for 1 hour. The precipitate is collected, washed twice, air dried and then resuspended in 10 μl H$_2$O. The BamHI digestion is carried out in substantial accordance with the foregoing teaching, except 10X BamHI restriction buffer (0.2M Tris-HCl pH 8.0, 1M NaCl, 70 mM MgCl$_2$ and 20 mM 2-mercaptoethanol) and 2 μl BamHI restriction enzyme are used instead of EcoRI enzyme and buffer. The mixture is then electrophoresed through an agarose gel and the cosmid backbone purified using standard, well-known techniques.

Ten milligrams of pBR322 is then double digested with EcoRI and BamHI in substantial accordance with the teaching in the preceding paragraph. An ~375 bp EcoRI-BamHI restriction fragment, which contains a portion of the tetracycline resistance gene, is gel-purified and ligated into the cosmid backbone and used to transform *E. coli* in substantial accordance with the teaching of Examples 2B and 2C. Transformants having ampicillin and tetracycline resistant, apramycin sensitive phenotypes are selected, and are then conventionally cultured for subsequent production and isolation of their cosmid DNA.

Next, the ~752 bp EcoRI-PstI fragment containing a portion of the ampicillin resistance gene present in the above-constructed intermediate cosmid was deleted. This deletion was performed in substantial accordance with the teaching of the preceding paragraphs, except 10X PstI restriction buffer (500 mM Tris-HCl pH 8.0, 100 mM MgCl$_2$ and 500 mM NaCl) and PstI restriction enzyme were used in place of BamHI restriction buffer and BamHI restriction enzyme. The cosmid backbone from this digestion was then purified using agarose gel electrophoresis. The apramycin resistance (Am$^R$) gene from plasmid pKC222 (the construction of which was disclosed in U.S. Pat. No. 4,559,302 and is hereby incorporated by reference) was isolated on an ~1500 bp EcoRI-PstI fragment in substantial accordance with the above-described procedures. This fragment was subcloned and replaced the aforementioned deleted EcoRI-PstI region of the intermediate cosmid. The resultant cosmid was designated as pKC473 and used to transform *E. coli* K12 DH1 (NRRL B-15021) in substantial accordance with the teachings of Examples 2B and 2C. The identity of the desired transformants was conventionally confirmed by initially selecting for the Tc$^R$ phenotype and then replicating those Tc$^R$ colonies to select for Am$^R$ colonies The resultant *E. coli* K12 DH1/pKC473 transformants were conventionally cultured for subsequent production and isolation of cosmid pKC473.

EXAMPLE 4
Construction of Cosmid Shuttle Vector pKC505

Figure 3:
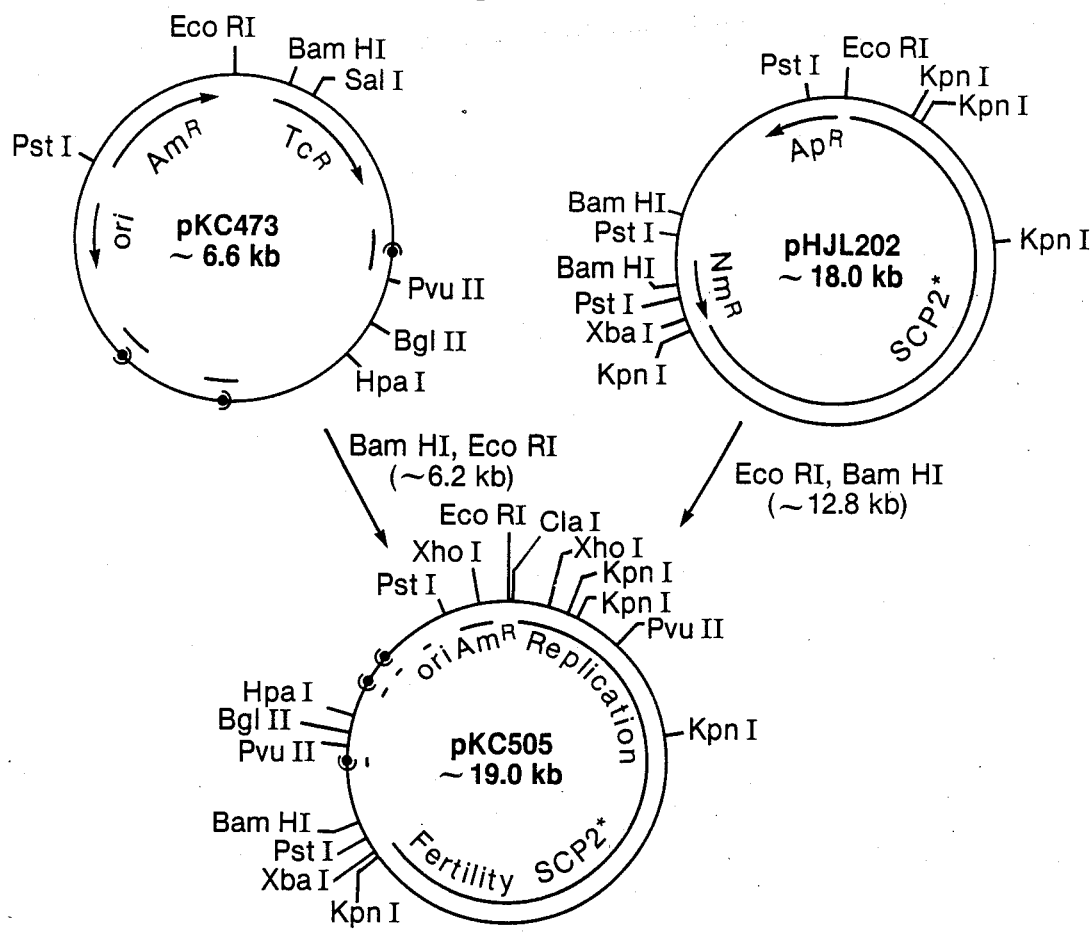
FIG. 3 is a flow chart illustrating the construction of cosmid pKC505.

Cosmid pKC505 was constructed from restriction fragments of cosmid pKC473 and plasmid pHJL202 in substantial accordance with the teaching of Example 3 and the flow chart in FIG. 3 of the accompanying drawings. Generally, the two vectors, pKC473 and pHJL202, were individually treated in a double digest reaction with BamHI and EcoRI restriction enzymes to generate linear fragments. These digestion products were mixed, the fragments ligated in substantial accordance with the teaching of Example 2B and then used to transform *Streptomyces ambofaciens*, selecting for apramycin resistance in substantial accordance with the teaching of Example 5. The resulting ~19 kb plasmid, designated pKC505, comprises the pKC473 vector backbone and an ~12.8 kb BamHI-EcoRI fragment encoding the SCP2* replication and fertility functions from plasmid pHJL202. This ~12.8 kb fragment replaced the ~375 bp in pKC473 fragment coding for the Tc$^R$ gene which was originally present. Cosmid pKC505 was subsequently shuttled into *E. coli*, back-transformed into *Streptomyces ambofaciens*, and then further characterized by restriction enzyme analysis.

EXAMPLE 5
Construction of *Streptomyces ambofaciens*/pKC505

About 1 μg of the DNA from Example 4 and 200 μl of protoplasts of *Streptomyces ambofaciens* (NRRL 15263) were mixed with 500 μl of 55% polyethylene glycol (Sigma) in P medium (Hopwood and Wright, 1978, *Molecular and General Genetics* 162:307), vortexed, and then aliquots of 25 μl and 250 μl were plated onto R2YE* plates with 3 ml of R2YE top agar. The plates were incubated for 18 hours at 30° C. and then overlayed with 3 ml of R2YE top agar containing sufficient apramycin** for a final concentration of 50 μg/ml. The plates were then incubated for an additional 3 days at 30° C. The identity of the desired transformants was conventionally confirmed by selecting for apramycin resistance. The resulting *S. am-*

*bofaciens*/pKC505 apramycin resistant colonies were isolated according to known procedures, cultured and used for production of cosmid pKC505 DNA. Cosmid pKC505 DNA was also transformed into *E. coli* for further characterization and verification.

| Sucrose | 103 g | Trace Element Mix | 2 ml |
|---|---|---|---|
| 2.5% K$_2$SO$_4$ | 10 ml | 0.5% KH$_2$PO$_4$ | 10 ml |
| MgCl$_2$ | 10.1 g | 1M CaCl$_2$ | 20 ml |
| Glucose | 10 g | Proline | 3 g |
| Casamino acids | 0.1 g | 0.25 M TES pH 7.2 | 100 ml |
| | | 10% Yeast Extract | 50 ml |

\* R2YE medium was prepared with the following composition per liter:
\*\* Antibiotic apramycin can be obtained from either Sigma, St. Louis, Missouri or Eli Lilly and Company, Indianapolis, Indiana.

EXAMPLE 6

The Construction of a Genomic Library

A. Preparation of the Vector pKC505 DNA

About 50 μg of vector pKC505 DNA was digested with 50 units (10 μl) of HpaI in 10 μl BSA, 10 μl 10X HpaI restriction buffer (200 mM Tris-HCl pH 7.4, 200 mM KCl and 100 mM MgCl$_2$) and 70 μl water at 37° C. for one hour. Complete digestion produced one band migrating at 18.7 kb on a 0.3% agarose gel. The DNA was extracted with an equal volume of phenol saturated with TE, then with Sevag and precipitated with ethanol (three volumes). After 10 minutes of centrifugation in an Eppendorf centrifuge, the DNA was redissolved in 100 μl of water, to which 20 μl of 10X BAP buffer (0.5M Tris-HCl pH 8.0, 0.5M NaCl) and 80 μl of bacterial alkaline phosphatase (BAP, 24 μ/ml) were added. Dephosphorylation was done for one hour at 70° C. The DNA was extracted and precipitated as before and dissolved in 50 μl of 5 mM NaCl. The DNA was then digested with 50 units (5 μl) of BamHI in 10 μl BSA, 10 μl 10X BamHI restriction buffer (200 mM Tris HCl pH 8.0, 1M NaCl and 70 mM MgCl$_2$) and 75 μl water at 37° C. for two hours. Complete digestion produces two band S at 16.7 kb and 2.0 kb. The DNA was again extracted with phenol, Sevag, precipitated with ethanol and dissolved in 50 μl of TE. About 0.5 μg of DNA can be used in a ligase reaction to check the ligatability of the BamHI ends. Ligation produces 3 bands at 33.4 kb, 18.7 kb, and 4.0 kb.

B. Preparation of the Insert DNA

About 2.5 ml of fresh overnight culture of *Streptomyces ambofaciens* was used to inoculate 50 ml of TSB (Trypticase Soy Broth\*). The culture was grown overnight at 30°–32° C. with vigorous shaking. The cells were harvested by centrifugation, suspended in 10 ml lysis buffer (15% Sucrose, 25 mM Tris-HCl pH 8.0, 50 mM EDTA) plus lysozyme (5 mg/ml) and incubated at 37° for 15 minutes. Then, 0.1 ml of 10 mg/ml Proteinase K (prepared fresh in lysis buffer) was added, along with 1.0 ml of 10% sodium dodecyl sulfate (SDS). This mixture was immediately incubated at 70° C. for 15 minutes and then cooled on ice. Next, 2.5 ml of 5M potassium acetate was added and mixed by gentle inversion before placing on ice for 15 minutes. After gently extracting the material with TE saturated phenol, the layers were separated by centrifugation (10,000 rpm for 10 minutes) and the aqueous phase was transferred to a fresh tube using a pipet with the tip broken off. After gently extracting the material with an equal volume of Sevag, the layers were again separated, the aqueous phase transferred to a fresh tube and the DNA precipitated ethanol (two volumes) at room temperature. The precipitate was washed with 70% ethanol and then dissolved in 5 ml of TE. RNase A (final concentration of 50 μg/ml) and RNase T1 (final concentration of 1 μg/ml) were added and this solution was incubated at 37° C. for 30 minutes. After extracting twice with phenol, twice with Sevag and then precipitating with ethanol (two volumes), the DNA was dried in vacuo and redissolved in TE (in 1 ml for a 50 ml culture). The DNA was sized on a 0.3% agarose gel and was found to have an average size of 70 kb.

Next, 200 μg of *Streptomyces ambofaciens* chromosomal DNA were incubated with 85 units (10 μl) of MboI in 100 μl BSA, 100 μl MboI restriction buffer (500 mM Tris-HCl pH 8.0, 100 mM MgCl$_2$, 50M NaCl) and ~800 μl water at 37° C. for three minutes. This particular condition was found, empirically, to give the desired suitable distribution of partially digested DNA. The DNA was extracted with phenol, Sevag, and precipitated with ethanol (1/10 volume of 3M NaOAc, three volumes ethanol at −70° C. for 30 minutes). The precipitate was collected by centrifugation (15 minutes) in an Eppendorf centrifuge and then the DNA was dissolved in 125 μl of water. After saving ~5 μg of DNA for use in determining whether the subsequently performed dephosphorylation was complete, the rest of the DNA was added to 20 μl of 10X bacterial alkaline phosphase (BAP) buffer and 80 μl (24 units/ml) of BAP. This mixture was incubated at 70° C. for one hour and then 80 μl of BAP was added and incubated for an additional hour. The DNA was extracted with phenol, Sevag, precipitated as taught directly above, and dissolved in 50 μl TE. The size of this DNA was estimated on a 0.3% agarose gel and was found to be ~30 kb.

\*TSB is made at 30 g/l and is obtained from Baltimore Biological Laboratories (BBL), P.O. Box 243, Cockeysville, Md. 21031.

C. Ligation of the Vector DNA to the Insert DNA

About 2 μl (approximately 1 μg) of vector pKC505 DNA that was HpaI-digested, dephosphorylated and BamHI-digested from Example 6A, along with 4 μl (approximately 1.2 μg) of donor DNA MboI partials that have been dephosphorylated from Example 6B, were ligated in a 10 μl reaction with 400 units of T4 DNA ligase in substantial accordance with the teaching of Example 2B, for 16 hours at 16° C. The ligation was monitored by running 5 μl of the ligation reaction mixture, along with unligated DNA controls, on a 0.3% agarose gel.

D. In Vitro Packaging

Packaging was performed by adding about 2.5 μl of the ligation mixture to the Gigapack\* freeze-thaw extract 10 μl)-containing tube. To this, 15 μl of the Sonic extract was added, the solution was gently mixed, centrifuged briefly and then incubated for two hours at room temperature (24° C.). To this mixture, about 0.5 ml of SM (100 mM NaCl, 10 mM MgSO$_4$, 50 mM Tris-HCl pH 7.5, 0.02% gelatin) and 25 μl of chloroform were added, mixed and centrifuged for one minute in an Eppendorf centrifuge to clarify. Chloroform was added to kill any living bacteria. The supernatant was used to infect *E. coli* cells.

\*Packaging kits are available from several manufacturers.
Gigapack Vector Cloning Systems, 3770 Tansy Street, San Diego, Calif. 92121
Promega Biotec, 2800 S. Fish Hatchery Road, Madison, Wis. 53711

E. Transduction of *E. coli* K12 SF8

*E. coli* K12 SF8 (NRRL B-15835) was inoculated into 5 ml of Tryptone yeast extract supplemented with 0.2% maltose and 10 mM magnesium sulfate (TYMM). The culture was incubated overnight at 37° C. without aeration. After 50 ml more TYMM were added to the overnight culture, the culture was incubated three hours at 37° C. with aeration. The cells were centrifuged at 6,000 rpm for five minutes and the pellet resuspended in three ml of TM (10 mM Tris-HCl pH 7.6, 10 mM $MgSO_4$).

About 0.2 ml each of the cells were infected with 10 $\mu$l or 50 $\mu$l of the in vitro packaged phage. Adsorption was done for 10 minutes at 37° C. Upon the addition of 1 ml of TY broth, the mixtures were incubated for two hours at 30° C. (All *E. coli* cultures pKC505 or its derivatives are grown at 30°–34° C. rather than at 37°–42° C.). Aliquots (0.1 ml) were plated on TY plates supplemented with 100 $\mu$g/ml apramycin and incubated overnight at 30° C. about 27 transductants/0.1 ml for the 10 $\mu$l packaged lysate and 130 transductants/0.1 ml for the 50 $\mu$l packaged lysate were obtained.

A scaled-up reaction was also performed with the remaining phage lysate. Thus, ~500 $\mu$l of phage lysate were added to 1.5 ml of TM in a 50 ml Erlenmeyer flask and shaken for 15 minutes at 30° C. to evaporate any remaining chloroform. The SF8 cells were prepared as taught above except that the pellet was resuspended in 0.5 ml TM. These cells were added to the phage and incubated at 37° C. for 10 minutes without shaking. Ten ml of TY broth were added and the cells were incubated at 30° C. for 90 minutes with shaking. After centrifugation (6,000 rpm for five minutes) the cells were resuspended in three ml of TM and plated (0.1 ml/plate) on 30 TY plates supplemented with apraymycin. The plates were incubated overnight at 30° C. Approximately 1,000 colonies/plate were obtained for a total of 30,000 colonies. The *E. coli* transformants were pooled to create a primary library, from which a primary plasmid pool was made.

F. Transformation of *Streptomyces griseofuscus*

From a fully grown overnight culture of *Streptomyces griseofuscus* (ATCC 23916), about 0.5 ml was used to inoculate 10 ml of TSB plus 0.5% glycine. After incubation at 34° C. for 24 hours, the culture was homogenized using a tissue grinder and 0.5 ml of this homogenate was used to inoculate a new 10 ml TSB with 0.5% glycine culture. This culture was also incubated at 34° C. for 24 hours. At this point the cells can be stored frozen at −70° C. The culture was next transferred to a fifteen ml sterile polystyrene centrifuge tube and spun at 5,000 rpm for 10 minutes. The recovered pellet was washed once with 10 ml of P medium and then repelleted. The pellet was washed with 10 ml of P medium with 1 mg/ml lysozyme and incubated at 30° C. for ½ hour. Protoplast formation can be monitored by taking small samples for observation under a phase contrast microscope to identify a sample containing spherical cells. The protoplasts were centrifuged as taught above, washed twice in P media, and then resuspended in 2 ml of P medium.

About 150 $\mu$l of protoplasts in an 1.5 ml Eppendorf tube were added to 2 $\mu$l of the primary plasmid pool DNA and gently mixed. Immediately, 100 $\mu$l of 50% polyethylene glycol (MW 1000 in P Medium) were added and allowed to sit for two minutes. Next, 100 $\mu$l of the transform mix in 4 ml of R2 top agar were plated on dried R2 plates and then incubated at 30° C. for 20 hours. After overlaying with R2 top agar containing enough apramycin to give a final concentration of 25 $\mu$g/ml, the plates were incubated at 30° C. Transformants appeared two to three days after the overlay and a total of about 5,000 apramycin resistant colonies were obtained.

Figure 1:
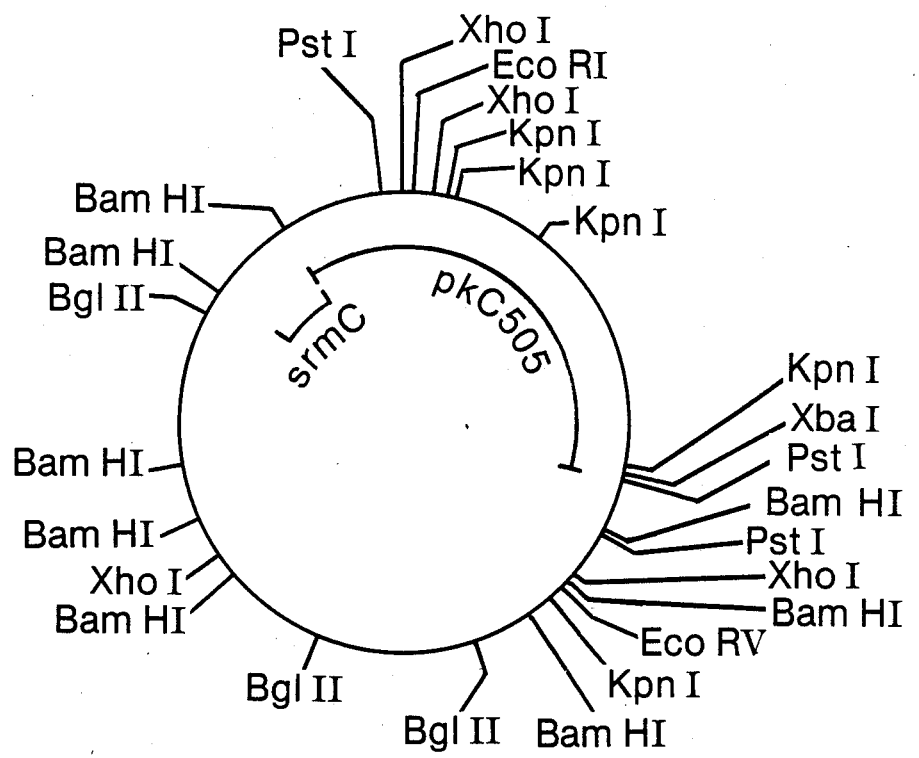
FIG. 1 shows the restriction site and function map of plasmid pKC592. For purposes of the present application, FIG. 1 and all subsequent figures are not drawn precisely to scale.

These colonies were scraped, pooled and grown in 1 liter TSB plus 100 g/ml apramycin overnight at 34° C. with shaking. About 100 ul of this culture was plated onto TSB agar supplemental with spiramycin (25 $\mu$g/ml). Transformants appeared after one week at 34° C. Twelve transformants were picked and grown in small volumes of TSB plus spiramycin. Rapid plasmid minipreps were made from these cells in substantial accordance with the teaching of Kieser, 1984, *Plasmid* 12:19. The plasmid DNA, designated as pKC592, was then analyzed by restriction enzyme analysis and shown to be uniform. A restriction site map of plasmid pKC592 is presented in FIG. 1 of the accompanying drawings.

EXAMPLE 7

Digestion of Cosmid pKC592 with BamHI And Isolation Of The ~2.9 Kb Fragment

About 1 $\mu$g of pKC592 DNA was digested with BamHI restriction enzyme in substantial accordance with the teaching of Example 3. This enzyme cleaved the insert in six distinct places, resulting in seven distinct fragments of ~1.5 Kb, ~1.7 Kb, ~1.8 Kb, ~2.1 Kb, ~2.9 Kb, ~5.5 Kb, and ~9.4 Kb. These fragments were isolated from AGE gels according to standard well-known procedures and the ~2.9 Kb fragment was shown to contain the desired spiramycin resistance gene.

EXAMPLE 8

Culture of *E. coli* K12 C600$R_k M_k$-/pHJL225 and Isolation of Plasmid DNA

Figure 4:
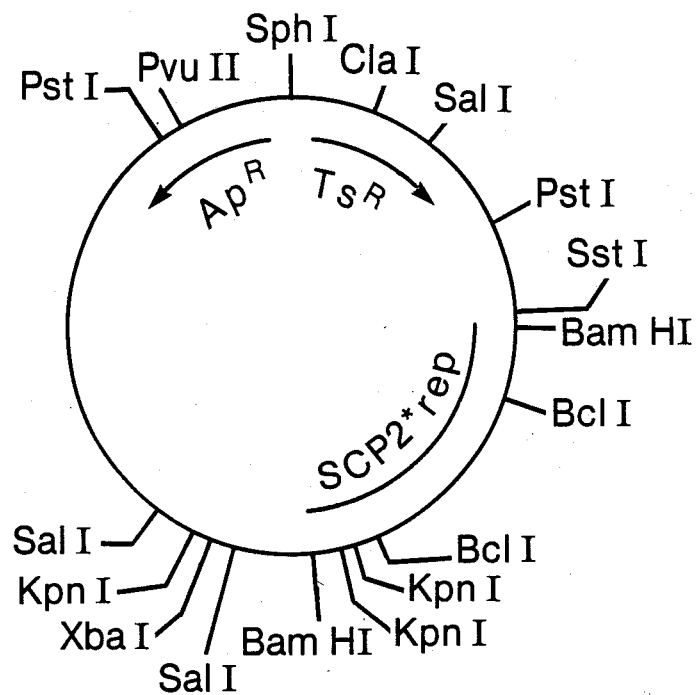
FIG. 4 shows the restriction site and function map of plasmid pHJL225.

The desired culture and subsequent isolation of plasmid pHJL225 was carried out in substantial accordance with the teaching of Example 1. The strain *E. coli* K12 C600$R_k M_k$-/pHJL225 is available to the public, as a preferred source and stock reservoir of the plasmid, under the accession number NRRL B-18052. A restriction site and function map of plasmid pHJL225 is presented in FIG. 4 of the accompanying drawings.

EXAMPLE 9

Construction of Moderate Copy Number Plasmids pHJL400 and pHJL401

A. NdeI Digestion of Plasmid pUC19

About 1 $\mu$g of plasmid pUC19 (Pharmacia, Inc., 800 Centennial Dr., Piscataway, N.J. 08854) was digested to completion in substantial accordance with the teaching of Example 3 using NdeI restriction enzyme and 10X NdeI restriction buffer (500 mM Tris-HCl pH 8.0, 100 mM $MgCl_2$ and 500 mM NaCl) to create linear vector fragments. After precipitation and washing, these linear fragments were dephosphorylated using calf intestine alkaline phosphatase in substantial accordance with the teaching of Maniatis et al., 1982.

B. Construction of Intermediate Plasmid pHJL399

About 35 $\mu$l (17.5 g) of plasmid pHJL225 (isolated in Example 8) were digested with BamHI restriction enzyme to completion in substantial accordance with the teaching of Example 3, and the desired ~2.2 kb BamHI fragment, which contains the SCP2* replicon, was purified by AGE. Next, about 20 µl (10 g) of plasmid pIJ702 (ATCC B-39155) were digested in substantial accordance with the teaching of Example 3, except 10 Units of BclI restriction enzyme and 10X BclI restriction buffer (500 mM Tris-HCl pH 8.0, 100 mM MgCl$_2$ and 500 mM NaCl) were used. The ~1.1 kb BclI fragment, which contains the thiostrepton resistance-conferring gene was isolated and purified by AGE. These two fragments were then ligated together in substantial accordance to the teaching of Example 2B to construct plasmid pHJL399, which was transformed into *Streptomyces lividans* TK23 (NRRL 15826) in substantial accordance to the teaching of Example 6F. The transformants were analyzed by restriction enzyme analysis of their constituent plasmids and then the plasmid pHJL399 DNA was isolated for use in the construction of plasmids pHJL400 and 401.

C. NdeI Digestion of Plasmid pHJL399 and Ligation of fragments

About 30 µl (1 µg) of plasmid pHJL399 were digested with NdeI restriction enzyme in substantial accordance with the teaching of Example 9A. Since there is a unique NdeI site in plasmid pHJL399, a single, linear fragment was generated and purified by AGE. This vector backbone was then ligated to the NdeI digested, dephosphorylated pUC19 fragments (isolated in Example 9A) in substantial accordance with the teaching of Example 2B.

D. Transformation of Escherichia coli JM109

Figure 5:
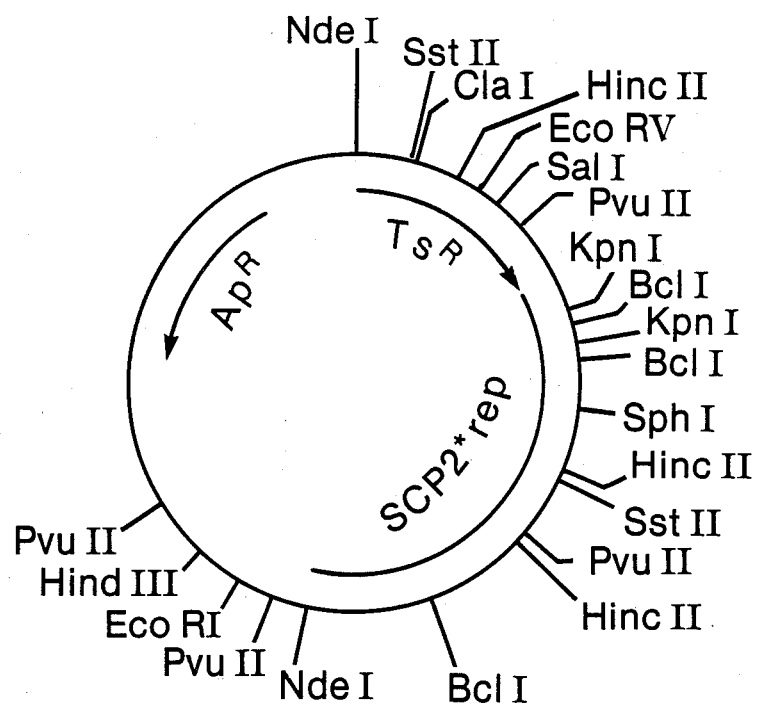
FIG. 5 shows the restriction site and function map of plasmid pHJL400.

Competent *E. coli* JM109 cells (Stratogene*) were transformed with the above ligation mixture using the calcium chloride/rubidium chloride procedure essentially as described in Maniatis et al., 1982. Transformants were identified by resistance to ampicillin and formation of blue colonies on media containing X-gal and verified by restriction digests of plasmid DNA. Plasmid pHJL401 contains the thiostrepton resistance-conferring fragment from pHJL399 near the ampicillin resistance gene, while pHJL400 contains the thiostrepton resistance-conferring fragment farther from the ampicillin resistance gene. Both plasmids transform *S. griseofuscus* and *S. lividans* to thiostrepton resistance. A diagram of plasmid pHJL400 is presented in FIG. 5 of the accompanying drawings.

EXAMPLE 10

Construction of Plasmid pKC631

About 10 µl (1 µg) of pHJL400 was digested with BamHI restriction enzyme in substantial accordance with the teaching of Example 3. About 0.1 µg of BamHI-digested DNA from pKC592 (isolated in Example 7) was then ligated into pHJL400 in substantial accordance with the teaching in Example 2B. Competent *E. coli* JM109 cells (Stratogene*) were then transformed using this ligation mix in substantial accordance with the teaching of Example 9D, selecting for ampicillin resistance. The transformants were pooled to make plasmid DNA in substantial accordance with the teaching of Example 1 and the pooled DNA was then transformed into *S. griseofuscus*. Transformation was carried out in substantial accordance with the teaching of Example 6F, selecting for thiostrepton resistance, and the transformants were pooled and grown in TSB supplemented with 25 µg/ml of spiramycin. After the culture had grown, the cells were plated on TSA with 25 µg/ml thiostrepton and plasmid DNA was isolated from spiramycin-resistant colonies that came up on the plate. This plasmid DNA was used to transform *E. coli* JM109 cells with selection for ampicillin resistance. White colonies were picked and the plasmid DNA was analyzed. All of the clones analyzed had the same plasmid and one of these, designated pKC631, was transformed into *S. griseofuscus* selecting for thiostrepton and then spiramycin resistance. A restriction site map of plasmid pKC631 is presented in FIG. 6 of the accompanying drawings.

*Stratogene, 3770 Tansy Drive, San Diego, Calif. 92121

EXAMPLE 11

Construction of plasmid pKC681

Figure 7:
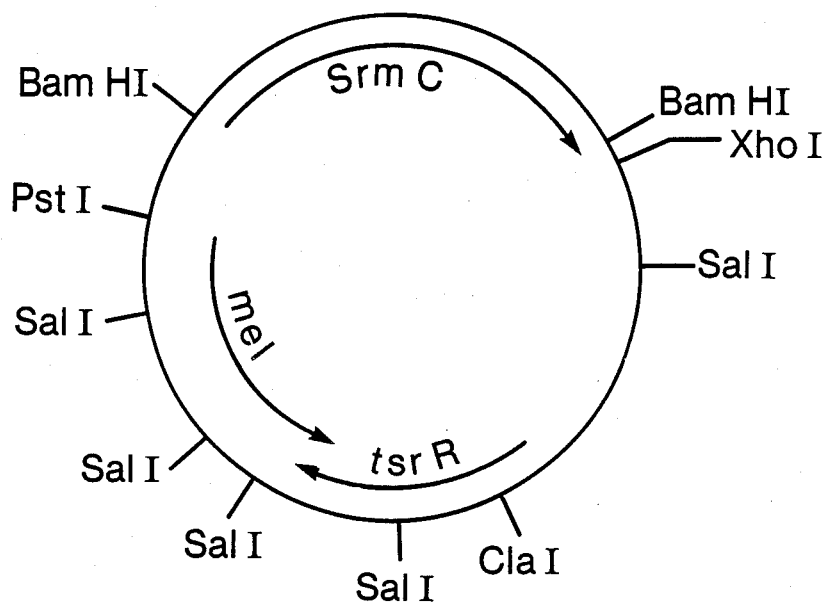
FIG. 7 shows the restriction site and function map of plasmid pKC681.
Figure 8:
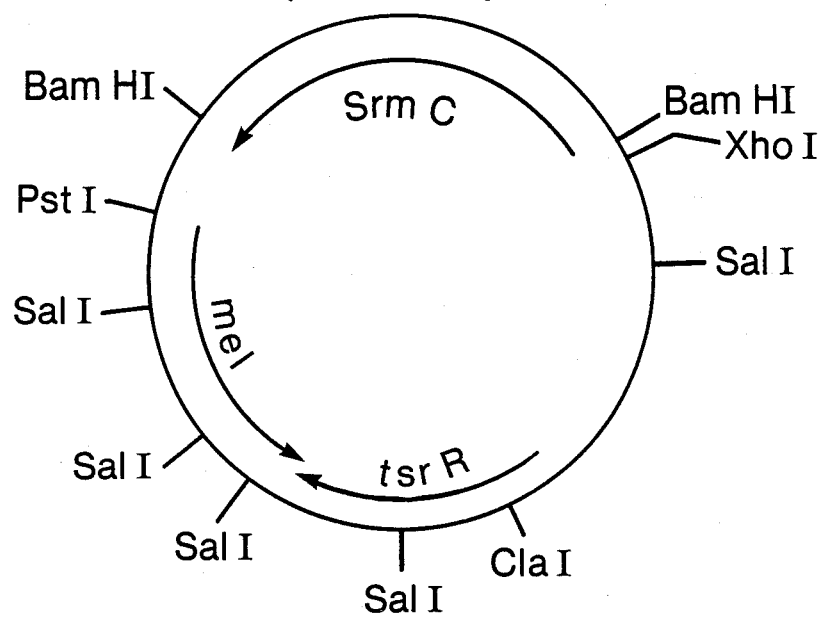
FIG. 8 shows the restriction site and function map of plasmid pKC682.

About 1 µg of pIJ702, isolated from *Streptomyces lividans* (ATCC 39155) in substantial accordance with the teaching of Kieser, 1984, *Plasmid* 12:19, 25 µl water, 5 µl BSA (1 mg/ml), 5 µl 10X BamHI restriction buffer (200 mM Tris-HCl pH 8.0, 1M NaCl, 70 mM MgCl$_2$ and 20 mM 2-mercaptoethanol) and 2 µl (~20 units) BamHI enzyme are mixed and incubated at 37° C. for 1 hour. This vector DNA is then precipitated, ~2.9 kb spiramycin resistance-conferring fragment of pKC592 (isolated in Example 7) is then ligated into the vector and transformed into *Streptomyces griseofuscus* in substantial accordance with the teachings of Examples 2B and 6F. The resultant plasmids pKC681 and pKC682, which differ only in the orientation of the srmC gene, confer spiramycin resistance to *Streptomyces griseofuscus*. A restriction site map of plasmids pKC681 and pKC682 are illustrated in FIGS. 7 and 8 of the accompanying drawings.

EXAMPLE 12

Construction of Integrating plasmid pKC1001

Chromosomal DNA is isolated from *Streptomyces fradiae* (ATCC 19609) in substantial accordance with the teaching of Example 6B, then the 5' overhang is filled using the DNA Polymerase I procedure essentially as described in Maniatis et al., 1982. About 2 µg of pBR322 (BRL) are then digested to completion using EcoRI restriction enzyme in substantial accordance with the teaching of Example 3 and then the 5' overhang of this EcoRI-cut pBR322 is filled in using the above mentioned DNA polymerase I procedure. The MboI-cut, filled-in chromosomal DNA and the EcoRI-cut, filled-in pBR322 are then ligated together in substantial accordance with the teaching of Example 2B. The ligation mix is transformed into competent *E. coli* JM109 cells in substantial accordance with the teaching of Example 9D, selecting for tetracycline resistance. This intermediate plasmid, pKC1001A, is then extracted from the transformed cells in substantial accordance with the procedure of Example 1.

About 10 µl (~5 µg) of plasmid pKC1001A, 25 µl water, 5 µl BSA, 5 µl 10X BamHI restriction buffer (200 mM Tris-HCl pH 8.0, 1M NaCl, 70 mM MgCl$_2$ and 20 mM 2-mercaptoethanol) and 1 µl BamHI enzyme are mixed and incubated at 37° C. for 45 minutes. A 10 µl aliquot is removed, mixed with 40 µl water and heated at 70° C. for 10 minutes to inactivate the enzyme. This protocol produces all possible reaction products ranging from molecules that have not been cleaved by the BamHI restriction enzyme to those that have been completely digested by the BamHI restriction enzyme. The aliquot is precipitated with 1/10 volume 3M NaOAc pH 8.0 and 2 volumes ethanol and then frozen at −70° C. for 1 hour. This partially BamHI digested plasmid is then ligated to the BamHI inserts from cosmid pKC592 (isolated in Example 7) in substantial accordance with the teaching of Example 2B. This ligation mixture is then transformed into *E. coli* JM109 cells and the transformants are selected for ampicillin and tetracycline resistance. All transformants are pooled and the plasmid DNA is extracted in substantial accordance with the teaching of Example 1. The resultant plasmids, designated pKC1001 and pKC1002 differ only in respect to the orientation of the srmC fragment, and are illustrated respectfully in FIGS. 9 and 10 of the accompanying drawings.

About 2 μl of plasmid pKC1001 is used to transform *Streptomyces fradiae* protoplasts in substantial accordance with the teaching of Example 6F, except the protoplasts are overlain with R2 top agar containing enough spiramycin to give a final concentration of 25 μg/ml. Plasmid pBR322 does not contain a *Streptomyces replicon*, so the only resistant colonies which arise are those in which the cells have undergone a crossover, homologous recombination and subsequent integration of the srmC gene into the *Streptomyces genome*.

EXAMPLE 13

Culture of *E. coli* K12 BE447/pKC331 and Isolation of Phasmid pKC331

A. Culture of *E. coli* K12 BE447/pKC331

A 2 ml culture of *E. coli* K12 BE447/pKC331 (NRRL B-15828) was grown in the presence of 50 μg/ml ampicillin in TY media (1% tryptone, 0.5% NaCl and 0.5% yeast extract, pH 7.4) until the cells reached stationary phase. The 2 ml culture was then used to inoculate a flask containing 1 liter of TY media containing 50 μg/ml ampicillin and growth continued until the optical density of the culture at 550 nanometers was between 0.50 and 0.75 absorbance units. When the O.D. 550 reached the 0.50–0.75 range, 1 g of uridine was added, and, 15 minutes later, 170 mg of chloramphenicol was added. The incubation and culturing was then continued for 16 hours.

B Isolation of Phasmid pKC331

The culture was centrifuged and the cell pellet resuspended in 10 ml of a solution that was 25% w/v sucrose; 50 mM Tris-HCl, pH 8; and 1 mM EDTA. Next, 2 ml of 0.5 M EDTA and 2 ml of a 5 mg/ml lysozyme solution in 0.25 M Tris-HCl, pH 8 were added, and the resultant mixture was incubated at room temperature for 15 minutes. After incubation, about 14 ml of a solution that was 50 mM Tris-HCl, pH 8; 6 mM EDTA; and 0.1% Triton X-100 were added. The lysozyme-treated cells were then mixed by inversion.

The lysed cell mix was centrifuged until the cell debris formed a loose pellet. After the cell debris pellet was discarded and the supernatant extracted with buffered (pH 8) phenol, the aqueous phase was made 0.25 M in NaCl and two volumes of ethanol were added. The resultant mixture was chilled to −70° C., and the nucleic acid was pelleted by centrifugation. Further centrifugation (45,000 rpm for 16 hours at 20° C.) using cesium chloride gradients with ethidium bromide was carried out to purify the phasmid DNA. The desired phasmid pKC331 DNA was then collected and the ethidium bromide and cesium chloride removed by conventional procedures. The approximately 1 mg of phasmid pKC331 DNA obtained by this procedure was dissolved in 1 ml of TE buffer (10 mM Tris-HCl, pH 8 and 1 mM EDTA) and stored at −20° C. A restriction site and function map of phasmid pKC331 is presented in FIG. 11 of the accompanying drawings.

EXAMPLE 14

Construction of Phage pKC1003

A. PstI Digestion of Phasmid pKC331 and Isolation of the ~37 kb PstI Restriction Fragment About 10 μg (10 μl) of the phasmid pKC331 isolated in Example 13 are added to 10 μl 10X PstI salts, 2 μl restriction enzyme PstI (~10 Units) and 78 μl H₂O. After gentle mixing, the digest is allowed to react 2 hours at 37° C. and after digestion, the ~37 kb PstI fragment containing the phage φC31 sequences is purified by conventional electrophoretic gel means. The purified fragment obtained (~5 μg) is suspended in 5 μl of TE buffer.

B Polymerase I Treatment and Ligation of the ~2.9 Kb Spiramycin Resistance-Conferring BamHI Restriction Fragment to the ~37 Kb Pst I Restriction Fragment of Phasmid pKC331

The 5' overhangs on both ends of the ~37 Kb PstI restriction fragment of phasmid pKC331 and the ~2.9 Kb BamHI spiramycin-resistance conferring fragment of pKC592 (isolated in Example 7) are filled in using the DNA Polymerase I procedure essentially as described in Maniatis et al., 1982. These fragments are then ligated together in substantial accordance with the teaching of Example 2B. This ligation produces desired phages pKC1003 and pKC1004, which differ only in respect to the orientation of the ~2.9 Kb srmC fragment (see FIGS. 12 and 13). The ligated DNA is used to transform Streptomyces to obtain infective phage particles and the phage are then used to prepare spiramycin-resistant Streptomyces via chromosomal integration of the vector.

EXAMPLE 15

Construction of *Streptomyces lividans*/pKC1003

A. List of Solutions

The following solutions are referred to throughout Example 15 and are presented here for clarity.

| 1. TSB (Trypticase Soy Broth) |
|---|
| TSB is made at 30 g/l and is obtained from Bethesda Research Laboratories, Inc., 8717 Grovemont Circle, P. O. Box 577, Gaithersburg, Maryland 20760. |
| 2. YMX agar |
| 0.3% yeast extract |
| 0.3% malt extract |
| 0.2% Dextrose |
| 2.0% agar |

| 3. P medium (~100 ml) | |
|---|---|
| Ingredient | Amount |
| Sucrose | 10.3 g |
| K₂SO₄ | 0.025 g |
| Trace element solution (see #4) | 0.2 ml |
| MgCl₂ · 6H₂O | 0.203 g |
| Water | to 80 ml |
| After autoclaving add: | |
| KH₂PO₄ (0.5%) | 1 ml |
| CaCl₂ · 2H₂O (3.68) | 10 ml |
| (N—tris(hydroxymethyl)- | 10 ml |

-continued

| Ingredient | Amount |
| --- | --- |
| methyl-2-aminoethane sulfonic acid) "TES" Buffer, 0.25 M, pH 7.2 | |

4. Trace element solution (~1 l):

| Ingredient | Amount |
| --- | --- |
| $ZnCl_2$ | 40 mg |
| $FeCl_2 \cdot 6H_2O$ | 200 mg |
| $CuCl_2 \cdot 2H_2O$ | 10 mg |
| $MuCl_2 \cdot 4H_2O$ | 10 mg |
| $Na_2B_4O_7 \cdot 10H_2O$ | 10 mg |
| $(NH_4)_6MO_7O_{24} \cdot 4H_2O$ | 10 mg |

5. Regeneration Medium (~1 l):

| Ingredient | Amount |
| --- | --- |
| Sucrose | 103 g |
| $K_2SO_4$ | 0.25 g |
| Trace element solution | 2 ml |
| $MgCl_2 \cdot 6H_2O$ | 10.12 g |
| glucose | 10 g |
| L-asparagine. 1 $H_2O$ | 2.0 g |
| casamino acids | 0.1 g |
| Agar | 22 g |
| Water | to 700 ml |
| After autoclaving add: | |
| $KH_2PO_4$ (0.05 g/100 ml) | 100 ml |
| $CaCl_2$ (2.22 g/100 ml) | 100 ml |
| TES Buffer (5.73 g/100 ml, pH 7.2) | 100 ml |
| NaOH (5N) | 1 ml |

6. R2YE medium is R2 medium with 20 ml of 25% Yeast Extract added per liter.

B. Growth of Cultures for Preparation of Protoplasts

A vegetative inoculum was conventionally prepared by growing *Streptomyces lividans* 1326 (ATCC 15825) under submerged conditions for 20 hours at 30° C. in TSB supplemented with 0.4% glycine. The procedure for protoplasting *S. lividans* is generally performed as follows. A culture of *S. lividans* was spread on a plate containing YMX agar and incubated at 30° C. for approximately 48 hours. A single bacterial colony from the plate was then inoculated into 10 ml TSB; the culture was homogenized and then incubated at 30° C. overnight. About 4 ml of the overnight culture were homogenized, added to 100 ml TSB supplemented with 0.4% glycine and then incubated overnight at 30° C. This procedure was repeated, using the fresh overnight culture. About 50 ml of 50% (v/v) glycerol were then added to the culture and 15 ml samples were frozen and stored for up to six months at −20° C. The frozen cells were thawed by placing the tube at room temperature in a beaker of water. The cells were then harvested in a bench top centrifuge and washed three times in 10 ml of 10.3% sucrose. The cell pellet was resuspended in 10 ml of P medium supplemented with lysozyme (1 mg/ml) and incubated at 30° C. for 2 hours. The mixture was then centrifuged to pellet the protoplasts. The pellet was washed three times, using 10 ml P medium and vortexing the pellet into solution each wash. The protoplasts were resuspended in 2 ml P medium for subsequent transformation.

C. Transfection of *Streptomyces lividans*

The ligated DNA of Example 14, 200 μl of *Streptomyces lividans* protoplasts, $10^8$ spores of *Streptomyces lividans* and 500 μl of 55% polyethylene glycol in P medium are vortexed and aliquots of 25 μl and 250 μl are plated onto R2YE plates with 3 ml of R2YE top agar. The plates are incubated at 37° C. Plaques can usually be seen after ~20 hours. After plaques appear, they are removed from the plate and the phage particles washed off the agar into TSB medium. Serial dilutions of the phage suspension are made and aliquots removed and mixed with $10^8$ spores of *Streptomyces lividans*. These dilutions are made in order to achieve a good plaque distribution on the plate. The mixtures are plated on R2YE plates and incubated at 30° C. until sporulation occurs, a process taking about 4 days. After sporulation, the plates are replica plated onto fresh R2YE plates containing 25 μg/ml spiramycin. The replica plates are then incubated at 30° C. for 3-4 days, and the resultant *S. lividans*/pKC1003 spiramycin-resistant colonies are isolated, cultured and identified according to known procedures.

Representative transfectants constructed in accordance with the foregoing teaching include, but are not limited to, the following transfectants listed in Table XI.

Table XI

Representative Transfectants

1. Streptomyces R/R[1] wherein R is *fradiae, griseofuscus* and *lividans* and wherein R[1] independently is pKC1003 and pKC1004.

I claim:

1. A recombinant DNA cloning vector which comprises
   (a) a DNA sequence selected from the group consisting of an origin of replication and integration sequence,
   (b) a spiramycin C resistance gene srm C of *Streptomyces ambofaciens* that confers resistance to the antibiotic spiramycin, subject to the limitation that said origin of replication and integration sequence are functional in Streptomyces and Nocardia.

2. The vector of claim 1 which is a plasmid.

3. A plasmid of claim 2 selected from the group consisting of plasmids pKC681 and pKC682.

4. The plasmid of claim 3 that is plasmid pKC681.

5. The plasmid of claim 3 that is plasmid pKC682.

6. A plasmid of claim 2 which is capable of integrating into the genome of Streptomyces.

7. The vector of claim 1 that is a phage.

8. A phage of claim 7 that is selected from the group consisting of phages pKC1003 and pKC1004.

9. The recombinant DNA cloning vector of claim 1 which further comprises
   (a) an *Escherichia coli* origin of replication; and
   (b) a DNA sequence that confers a selectable phenotype in *Escherichia coli*.

10. The vector of claim 9 which is a plasmid.

11. A plasmid of claim 10 that is selected from the group consisting of plasmids pKC592 and pKC631.

12. The plasmid of claim 11 that is plasmid pKC592.

13. The plasmid of claim 11 that is plasmid pKC631.

14. The constructed recombinant DNA sequence comprising the srmC gene of *Streptomyces ambofaciens*.

15. The ~2.9 Kb BamHI restriction fragment of plasmid pKC592.

16. A host cell transformed with a recombinant DNA cloning vector of claim 1.

17. A host cell transformed with a plasmid of claim 2.

18. A host cell transformed with a plasmid of claim 6.

19. A host cell transfected with a phage of claim 7.

20. A host cell transformed with a recombinant DNA cloning vector of claim 9.

21. A host cell transformed with a plasmid of claim 10.

22. A host cell of claim 21 that is selected from the group consisting of *Streptomyces, Nocardia* and *Escherichia coli.*

23. The transformed host cell of claim 22 which is *Streptomyces.*

24. The transformed host cell of claim 22 which is *Nocardia.*

25. The transformed host cell of claim 22 which is *Escherichia coli.*

26. The transformed host cell of claim 23 which is *Streptomyces griseofuscus*/pKC592.

27. The transformed host cell of claim 23 which is *Streptomyces griseofuscus*/pKC631.

28. The transformed host cell of claim 25 which is *Escherichia coli*/pKC592.

29. The transformed host cell of claim 25 which is *Escherichia coli*/pKC631.

* * * * *